(12) United States Patent
Padsalgikar et al.

(10) Patent No.: US 8,882,832 B2
(45) Date of Patent: Nov. 11, 2014

(54) IMPLANTABLE PROSTHESIS

(75) Inventors: Ajay D. Padsalgikar, Plymouth, MN (US); Frank Maguire, Salt Lake City, UT (US); Sriram Venkataramani, Draper, UT (US)

(73) Assignee: Aortech International plc (GB)

( * ) Notice: Subject to any disclaimer, the term of this patent is extended or adjusted under 35 U.S.C. 154(b) by 0 days.

(21) Appl. No.: 13/557,580

(22) Filed: Jul. 25, 2012

(65) Prior Publication Data

US 2013/0190870 A1    Jul. 25, 2013

Related U.S. Application Data

(60) Provisional application No. 61/513,211, filed on Jul. 29, 2011.

(51) Int. Cl.
*A61F 2/12* (2006.01)

(52) U.S. Cl.
USPC .................................. 623/8; 623/7; 427/2.24

(58) Field of Classification Search
CPC ....................................................... A61F 2/12
USPC .................. 623/7, 8, 23.64; 156/145; 427/2.4
See application file for complete search history.

(56) References Cited

U.S. PATENT DOCUMENTS

| 4,298,998 | A | * | 11/1981 | Naficy | 623/8 |
| 4,767,794 | A |   | 8/1988  | Modic et al. |  |
| 4,944,750 | A |   | 7/1990  | Cox, Jr. |  |
| 5,496,370 | A |   | 3/1996  | Hamas |  |
| 5,658,330 | A |   | 8/1997  | Carlisle et al. |  |
| 2009/0299472 | A1 | * | 12/2009 | Huang | 623/7 |

FOREIGN PATENT DOCUMENTS

| EP | 0322194 A1 | 6/1989 |
| EP | 2550942 A1 | 1/2013 |
| JP | 201331661 A | 2/2013 |
| WO | WO-9200338 A1 | 1/1992 |
| WO | WO-9813405 A1 | 4/1998 |
| WO | WO-9854242 A1 | 12/1998 |
| WO | WO-9903863 A1 | 1/1999 |
| WO | WO-9950327 A1 | 10/1999 |
| WO | WO-0064971 A1 | 11/2000 |
| WO | WO-2006034547 A1 | 4/2006 |
| WO | WO-2006114786 A2 | 11/2006 |
| WO | WO-2007112485 A1 | 10/2007 |
| WO | WO-2007121513 A1 | 11/2007 |
| WO | WO-2011006900 A1 | 1/2011 |

OTHER PUBLICATIONS

"European Application Serial No. 12178514.1, Extended European Search Report mailed Dec. 12, 2012", 9 pgs.

* cited by examiner

*Primary Examiner* — Thomas J Sweet
*Assistant Examiner* — Yashita Sharma
(74) *Attorney, Agent, or Firm* — Schwegman, Lundberg & Woessner, P.A.

(57) ABSTRACT

The invention relates to an implantable prosthesis and a shell for an implantable prosthesis and methods for making them, in particular a light weight implantable prosthesis containing a biocompatible filler which is suitable for use as a breast implant.

2 Claims, 1 Drawing Sheet

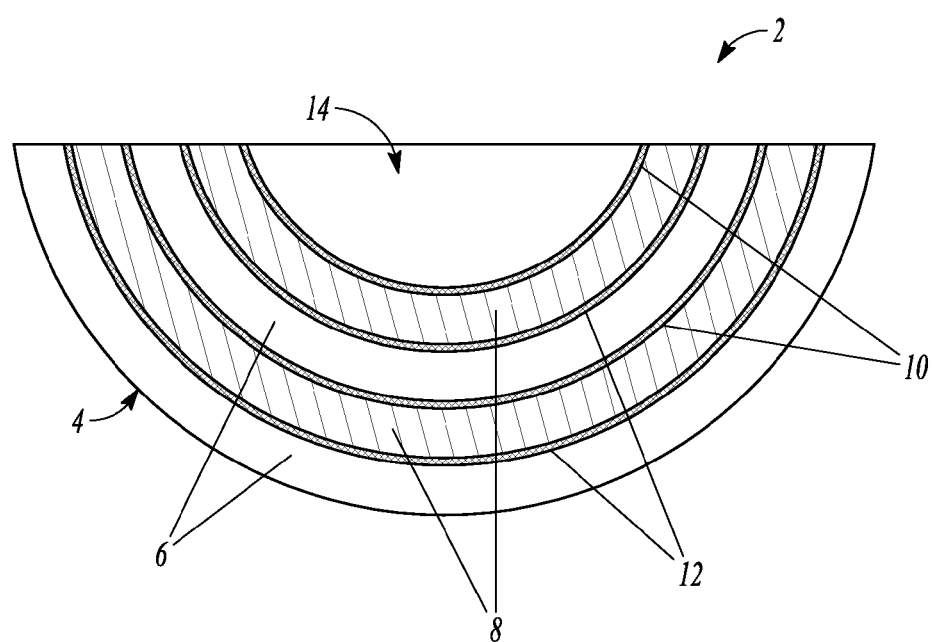

IMPLANTABLE PROSTHESIS

RELATED APPLICATION

This application claims the benefit of priority under 35 U.S.C. Section 119(e), to U.S. Provisional Application Ser. No. 61/513,211, filed Jul. 29, 2011, which application is incorporated herein by reference in its entirety.

FIELD

The invention relates to an implantable prosthesis and a shell for an implantable prosthesis and methods for making them, in particular a light weight implantable prosthesis containing a biocompatible filler which is suitable for use as a breast implant.

BACKGROUND

Reconstructive and cosmetic surgery is now common practice. Specifically cosmetic breast surgery has been developed to allow reconstruction of a woman's breast that was affected by procedures such as mastectomy. Cosmetic breast surgery has also become available to amend the appearance of a woman's breast, for example by adding an implant to increase the size of the breast, to correct asymmetries, change shape and fix deformities.

Generally the implant is required to be able to provide a specific form and maintain the form for many years, preferably for the lifetime of the woman in which the implant is installed to provide the need for additional invasive surgery. The implant is also required to have a specific feel preferably imitating the feel of a real breast. The implant also needs biodurable such that it is not ruined by interaction with the human body and it needs to be biocompatible so that the woman's health is not detrimentally affected by the implant under extreme circumstances, for example the implant is required to be non toxic in case of leakage from the implant.

The standard implants used today comprise an outer shell typically from vulcanised silicone or polyurethane, and an inner content typically formed form a silicone gel or saline. The specific weight of the commonly used filling materials is generally between 0.95 to 1.15 $g/cm^3$. An average implant may weigh between 50 to 1000 grams, or even more. The weight of the implant is an addition, which is not negligible for a person.

Over time breast implants are known to cause many problems, mostly related to the weight of the implant, for example, ptosis (i.e. sagging and deformity), breast tissue atrophy, prominence of the implant through breast tissue, back pain, and straie of the skin.

The use of salt to create porosity in silicone breast implant shells has been attempted. The porosity leading to a cellular structure of the shell has been created on the outside of the implant mainly to address issues with capsular contracture. This concept has also been used to offset density differences between the implant and breast tissue. Density differences lead to wrinkles and associated fold flaw failures in saline filled implants.

SUMMARY

It has been found that using porosity inside rather than outside of the shell and using a thick layer of the porous structure can lead to an effective weight reduction of implants. The 'foamed' shell can then be filled with the biocompatible filler as normal.

In one aspect, there is provided an implantable prosthesis comprising:
(i) an outer shell having an interior surface and an exterior surface, the exterior surface adapted to contact tissue in the body;
(ii) a biocompatible filler layer contained within the outer shell;
(iii) a foamed inner layer having an interior shell and an exterior shell which substantially prevent the pores of the foam being filled with the biocompatible filler, the foamed inner layer being contained within the biocompatible filler layer; and
(iv) repeating layers (ii) and (iii) one or more times if desired; and
(v) a biocompatible filler contained within the interior shell of the foamed inner layer.

In another aspect, there is provided a shell for an implantable prosthesis comprising:
(i) an outer shell having an interior surface and an exterior surface, the exterior surface adapted to contact tissue in the body;
(ii) a biocompatible filler layer contained within the outer shell; and
(iii) a foamed inner layer having interior shell and an exterior shell which substantially prevent the pores of the foam being filled with the biocompatible filler, the foamed inner layer being contained within the biocompatible filler layer; and
(iv) repeating layers (ii) and (iii) one or more times if desired.

In a further aspect there is provided a shell for an implantable prosthesis comprising:
(i) an outer shell having an interior surface and an exterior surface, the exterior surface adapted to contact tissue in the body;
(ii) a foamed inner layer having interior shell and an exterior shell which substantially prevent the pores of the foam being filled with biocompatible filler, the foamed inner layer being contained within the outer shell; and
(iii) repeating layer (iii) one or more times if desired.

Preferably the implantable prosthesis is lightweight. The term "lightweight" is used in the present context to refer to a prosthesis which achieves a weight reduction of up to 20% to 50% or more.

In a still further aspect, there is provided a method for making an implantable prosthesis defined above comprising
(i) forming an interior shell;
(ii) injecting a biocompatible filler into the interior shell;
(iii) coating the interior shell with a foamed inner layer;
(iv) coating the foamed inner layer with an exterior shell;
(v) repeating steps (i) to (iv) one or more times if desired;
(vi) coating the exterior shell of the foamed inner layer with an outer shell; and
(vii) injecting a biocompatible filler between the exterior shell of the foamed inner layer and the outer shell.

Each of the layers are preferably cured prior to coating of another layer. Insertion is preferably by injection.

The biocompatible filler is preferably a gel or a fluid and could be porous itself.

DETAILED DESCRIPTION

The present invention relates to an implantable prosthesis including (i) outer shell, (ii) a biocompatible filler contained within the outer shell, (iii) a foamed inner layer having an interior shell and an exterior shell which substantially prevent the pores of the foam being filled with the biocompatible filler, (iv) repeating layers (i) (iii) one or more times if desired and (v) a biocompatible filler contained within the foamed inner layer.

The present invention also relates to a shell for an implantable prosthesis including (i) an outer shell, (ii) a biocompatible filler contained within the outer shell, (iii) a foamed inner layer having an interior shell and an exterior shell which substantially prevent the pores of the foam being filled with the biocompatible filler and being capable of housing a biocompatible filler and (iv) repeating layers (i) and (iii) one or more times if desired.

The foamed inner layers result in the prosthesis and the shell being lightweight. The filler could also be porous which would also reduce the weight of the prosthesis.

The volume of the prosthesis and the space occupied by the filler can be calculated if it assumed that the prosthesis is hemispherical, the volume occupied by the filler will be as follows:

$$V = \frac{2}{3}\pi R^3$$

in which, R is the inner radius of the prosthesis. If the inner radius is decreased due to introduced porosity or foaming and the inner radius is taken as r, then the fraction of volume occupied by the filler, f will be as follows:

$$f = \left(\frac{r^3}{R^3}\right)$$

For a 9 cm prosthesis, a 1 cm porous structure on the prosthesis can lead to greater than 25% less volume for the filler to occupy. With the 'foamed' shell not adding a significant weight to the prosthesis, a layer of foam can result significant reduction in the overall weight of the prosthesis.

Implantable Prosthesis

The implantable prosthesis may be used in numerous locations in the body. While, the most common use is for restoring or improving on normal body contour or augmenting as well as reconstructing the female breast, it will be appreciated that the prosthesis may be implanted in other areas of the body, for example to replace or augment testicles, pectorals, a chin, cheeks, a calf, buttocks or other parts of the human or an animal body, while exhibiting tactile properties similar to natural tissue.

Outer, Interior and Exterior Shells

The outer, interior and exterior shells may be composed of the same or different materials such as a biocompatible silicon-containing material, for example, silicone or a silicon-containing polyurethane.

The term "silicone" as used herein refers to silicone or silicone based solids of varying hardness including elastomers, rubbers and resins. The hardness may be in the range of 10 to 90 Shore A. These polymers include silicons together with carbon, hydrogen and oxygen. Silicones are also known as polymerised siloxanes or polysiloxanes composed of units having the formula $(R)_2SiO$ in which R is an organic side chain which is not hydrogen. Representative examples are $[SiO(CH_3)_2]_n$ (polydimethylsiloxane) and $[SiO(C_6H_5)_2]_n$ (polydiphenylsiloxane) in which n is an integer of 1 or greater. The compounds can be viewed as a hybrid of both organic and inorganic compounds. The organic side chains confer hydrophobic properties while the —Si—O—Si—O— backbone is purely inorganic. Examples of silicones or silicone-based materials include silicone rubber, coatings, encapsulants and sealants.

The polyurethane is preferably biostable for use as a biomaterial in medical devices, articles or implants. Suitable biostable polyurethanes include polyurethanes, polyurethane ureas in particular polyurethanes, polyurethane ureas or polycarbonates containing silicon. Examples of silicon-containing polyurethanes, polyurethane ureas or polycarbonates include those disclosed in WO92/00338, WO98/13405, WO98/54242, WO99/03863, WO099/50327, WO00/64971 and WO2007/112485, the entire contents of which are incorporated herein by reference. The polyurethanes, polyurethane ureas or polycarbonates generally contain a soft segment and a hard segment. The segments can be combined as copolymers or as blends. For example, polyurethanes with soft segments such as PTMO, polyethylene oxide, polypropylene oxide, polycarbonate, polyolefin, polysiloxane (for example polydimethylsiloxane) and other polyether soft segments made from higher homologous series of diols may be used. Mixtures of any of the soft segments may also be used. The soft segments also may have either alcohol end groups or amine end groups. The molecular weight of the soft segments may vary from about 500 to about 6000. It will be understood that the molecular weight values referred to herein are "number average molecular weights".

Suitable polyether diol and diamine soft segments include those represented by the formula (I)

$$\text{A-}[(CH_2)_m\text{—O}]_n\text{-A'} \qquad (I)$$

in which
A and A' are OH or NHR wherein R is H or optionally substituted $C_{1-6}$ alkyl, more preferably optionally substituted $C_{1-4}$ alkyl;
m is an integer of 4 or more, preferably 4 to 18; and
n is an integer of 2 to 50.

Polyether diols of formula (I) wherein m is 4 to 10 such as polytetramethylene oxide (PTMO), polyhexamethylene oxide (PHMO), polyheptamethylene oxide, polyoctamethylene oxide (POMO) and polydecamethylene oxide (PDMO) are preferred. PHMO is particularly preferred.

The preferred molecular weight range of the polyether is 200 to 5000, more preferably 200 to 2000.

Suitable polycarbonate diols include poly(alkylene carbonates) such as poly(hexamethylene carbonate) and poly (decamethylene carbonate); polycarbonates prepared by reacting alkylene carbonate with alkanediols for example 1,4-butanediol, 1,10-decanediol (DD), 1,6-hexanediol (HD) and/or 2,2-diethyl 1,3-propanediol (DEPD); and silicon based polycarbonates prepared by reacting alkylene carbonate with 1,3-bis(4-hydroxybutyl)-1,1,3,3-tetramethyldisiloxane (BHTD) and/or alkanediols.

It will be appreciated when both the polyether and polycarbonate macrodiols are present, they may be in the form of a mixture or a copolymer. An example of a suitable copolymer is a copoly(ether carbonate) macrodiol represented by the formula (II)

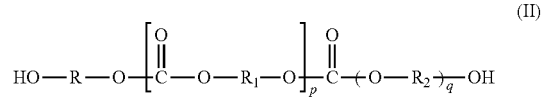
(II)

in which
$R_1$ and $R_2$ are the same or different and selected from an optionally substituted $C_{1-6}$ alkylene, $C_{2-6}$ alkenylene, $C_{2-6}$ alkynylene, arylene or a heterocyclic divalent radical; and
p and q are integers of 1 to 20.

Although the compound of formula (II) above indicates blocks of carbonate and ether groups, it will be understood that they also could be distributed randomly in the main structure.

Suitable polysiloxane diols or diamines are represented by the formula (III):

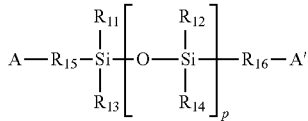

(III)

in which

A and A' are OH or NHR wherein R is H or optionally substituted $C_{1-6}$ alkyl, more preferably optionally substituted $C_{1-6}$ alkyl;

$R_{11}$, $R_{12}$, $R_{13}$ and $R_{14}$ are independently selected from hydrogen or optionally substituted $C_{1-6}$ alkyl;

$R_{15}$ and $R_{16}$ are the same or different and selected from optionally substituted $C_{1-6}$ alkylene, $C_{2-6}$ alkenylene, $C_{12-6}$ alkynylene, arylene or a heterocyclic divalent radical; and p is an integer of 1 or greater.

A preferred polysiloxane is a hydroxyl terminated PDMS which is a compound of formula (III) in which A and A' are hydroxyl, $R_{11}$ to $R_{14}$ are methyl and $R_{15}$ and $R_{16}$ are as defined above. Preferably $R_{15}$ and $R_{16}$ are the same or different and selected from propylene, butylene, pentylene, hexylene, ethoxypropyl ($-CH_2CH_2OCH_2CH_2CH_2-$), propoxypropyl and butoxypropyl, more preferably ethoxypropyl. A particularly preferred polysiloxane is Shin Etsu product X-22-160AS having a molecular weight of 947.12 which is α-ω-bis(hydroxyethoxypropyl)polydimethylsiloxane.

Other silicon-containing diols of the formula (III) are 1,3-bis(4-hydroxybutyl)tetramethyl disiloxane (BHTD) (compound of formula (III) in which A and A' are OH, $R_{11}$, $R_{12}$, $R_{13}$ and $R_{14}$ are methyl, $R_{15}$ and $R_{16}$ are butyl and $R_{17}$ is O), 1,4-bis(3-hydroxypropyl)tetramethyl disilylethylene (compound of formula (III) in which A and A' are OH, $R_1$, $R_{12}$, $R_{13}$ and $R_{14}$ are methyl, $R_{15}$ and $R_{16}$ are propyl and $R_{17}$ is ethylene) and 1-4-bis(3-hydroxypropyl)tetramethyl disiloxane, more preferably BHTD.

The polysiloxanes may be obtained as commercially available products such as X-22-160AS from Shin Etsu in Japan or prepared according to known procedures. The preferred molecular weight range of the polysiloxane macrodiol is 200 to 6000, more preferably from 200 to 5000.

Other preferred polysiloxanes are polysiloxane macrodiamines which are polymers of the formula (III) wherein A is $NH_2$, such as, for example, amino-terminated PDMS.

Suitable silicon-containing polycarbonates have the formula (IV):

in which $R_{11}$, $R_{12}$, $R_{13}$, $R_{14}$ and $R_{15}$ are as defined in formula (III) above;

$R_{16}$ is an optionally substituted $C_{1-6}$ alkylene, $C_{2-6}$ alkenylene, $C_{2-6}$ alkynylene, arylene or a heterocyclic divalent radical;

$R_{17}$ is a divalent linking group, preferably O, S or $NR_{18}$;

$R_{18}$ and $R_{19}$ are same or different and selected from hydrogen or optionally substituted $C_{1-6}$ alkyl;

A and A' are as defined in formula (III) above;

m, y and z are integers of 0 or more; and x is an integer of 0 or more.

Preferably z is an integer of 0 to 50 and x is an integer of 1 to 50. Suitable values for m include 0 to 20, more preferably 0 to 10. Preferred values for y are 0 to 10, more preferably 0 to 2.

A preferred silicon-containing polycarbonate is a compound of the formula (IV) in which A and A' are hydroxyl.

Particularly preferred silicon-containing polycarbonate diols are compounds of the formula (IV) in which A and A' are hydroxyl, $R_{11}$, $R_{12}$, $R_{13}$ and $R_{14}$ are methyl, $R_{18}$ is ethyl, $R_{19}$ is hexyl, $R_{15}$ and $R_{16}$ are propyl or $R_{14}$ butyl and $R_{17}$ is O or $-CH_2-CH_2-$, more preferably $R_5$ and $R_{16}$ are propyl when $R_{17}$ is O and $R_{15}$ and $R_{16}$ are butyl when $R_{17}$ is $-CH_2-CH_2-$. The preferred molecular weight range of the silicon-based polycarbonate macrodiol is from 400 to 5000, more preferably from 400 to 2000.

Preferably, the hard segment is formed from a diisocyanate and a chain extender.

The diisocyanate may be represented by the formula OCN—R—NCO, where —R— may be aliphatic, aromatic, cycloaliphatic or a mixture of aliphatic and aromatic moieties. Examples of diisocyanates include 4,4'-diphenylmethane diisocyanate (MDI), methylene biscyclohexyl diisocyanate ($H_{12}$ MDI), tetramethylene diisocyanate, hexamethylene diisocyanate, trimethylhexamethylene diisocyanate, tetramethylxylylene diisocyanate such as p-tetramethylxylene diisocyanate(p-TMXDI) or m-tetramethylxylene-diisocyanate (m-TMXDI), 4,4'-dicyclohexylmethane diisocyanate, dimer acid diisocyanate, isophorone diisocyanate (IPDI), metaxylene diisocyanate, diethylbenzene diisocyanate, decamethylene 1,10 diisocyanate, cyclohexylene 1,2-diisocyanate, trans-cyclohexylene-1,4-diisocyanate (CHDI), 2,4-toluene diisocyanate (2,4-TDI), 2,6-toluene diisocyanate, xylene diisocyanate, p-phenylene diisocyanate (p-PDI), m-phenylene diisocyanate (m-PDI), hexahydrotoylene diisocyanate (and isomers), naphthylene-1,5-diisocyanate (NDI), 1-methoxyphenyl 2,4-diisocyanate, 4,4'-biphenylene diisocyanate, 3,3'-dimethoxy-4,4'-biphenyl diisocyanate or 1,6-diisocyanatehexane (DICH), isomers or mixtures thereof. Preferably the diisocyanate is MDI.

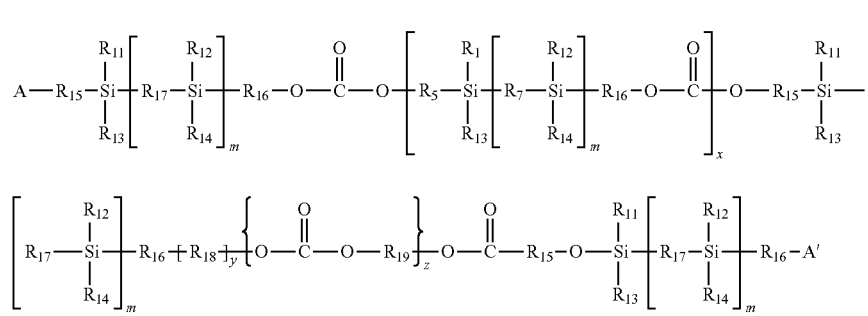

(IV)

The term "chain extender" in the present context means any chain extender which is capable of reacting with a diisocyanate group. The chain extender generally has a molecular weight range of 500 or less, preferably 15 to 500, more preferably 60 to 450 and may be selected from diol or diamine chain extenders.

Examples of diol chain extenders include $C_{1-12}$ alkane diols such as 1,4-butanediol (BDO), 1,6-hexanediol, 1,8-octanediol, 1,9-nonanediol, 1,10-decanediol and 1,12-dodecanediol; cyclic diols such as 1,4-cyclahexanediol, 1,4-cyclohexanedimethanol, 1,4-bis(2-hydroxyethoxy)benzene and p-xyleneglycol; and silicon-containing diols such as 1,3-bis(4-hydroxybutyl)tetramethyldisiloxane and 1,3-bis(6-hydroxyethoxypropyl)tetramethyldisiloxane.
Preferably the diol chain extender is BDO.

The diol chain extender may also contain silicon. Suitable silicon-containing diol chain extenders include those of formula (V)

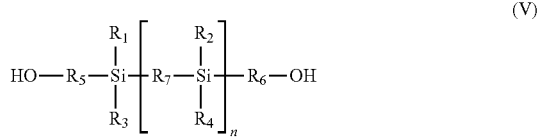

(V)

in which
$R_1$, $R_2$, $R_3$ and $R_4$ are the same or different and selected from H and an optionally substituted $C_{1-6}$alkyl;
$R_5$ and $R_6$ are the same of different and selected from optionally substituted $C_{1-6}$alkylene, $C_{2-6}$alkenylene, $C_{12-6}$alkynylene, arylene and a heterocyclic divalent radical;
$R_7$ is a divalent linking group, preferably O; and
n is 0 or greater, preferably 2 or less.

Suitable diamine chain extenders include $C_{1-12}$ alkane diamines such as 1,2-ethylenediamine, 1,3-propanediamine, 1,4-butanediamine and 1,6-hexanediamine; and silicon-containing diamines such as 1,3-bis(3-aminopropyl)tetramethyldisiloxane and 1,3-bis(4-aminobutyl)tetramethyldisiloxane, The diamine chain extender may also contain silicon. Suitable silicon-containing diamine chain extenders include those of formula (VI)

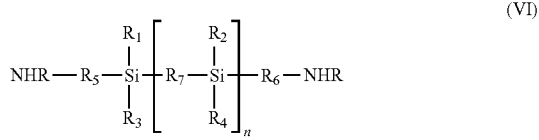

(VI)

in which
R is hydrogen or an optionally substituted $C_{1-6}$alkyl;
$R_1$, $R_2$, $R_3$ and $R_4$ are the same or different and selected from hydrogen and optionally substituted $C_{1-6}$alkyl;
$R_5$ and $R_6$ are the same or different and selected from optionally substituted $C_{1-6}$alkylene, $C_{2-6}$alkenylene, $C_{12-6}$alkynylene, arylene and a heterocyclic divalent radical;
$R_7$ is a divalent linking group, preferably O; and
n is 0 or greater, preferably 2 or less.

The outer shell serves as an enclosure for preventing the content of prosthesis from leaking out. Optionally the prosthesis may be provided in various shapes, for example round, oval, anatomical, custom or other and the outer shell may be smoothened or textured with various patterns.

The interior and exterior shells house the foamed inner layer and substantially prevent the pores of the foam from being filled with the biocompatible filler.

Foamed Inner Layer

The foamed inner layer is preferably an open celled low density foam and may be composed of the same materials as described above for the outer, interior and exterior shells. These materials can be made porous using any suitable known technique such as the use of a blowing agent for example water or alcohol which produces hydrogen and the hydrogen is trapped by the crosslinking of the biocompatible silicon-containing material. Examples of suitable low density silicone foams are disclosed in U.S. Pat. No. 4,767,794, the entire contents of which are incorporated herein by reference.

More than one foamed inner layer is advantageously present to result in a significant reduction in the overall weight of the prosthesis. The foamed inner layer is located between the interior and exterior shells.

Biocompatible Filler

The biocompatible filler may be a gel or a saline solution or a combination of both. When the filler is a gel it is typically a silicone gel including the silicon containing biostable gels described in WO2006/034547 or WO2007/121513.

The filler is contained within the interior shell of the foamed inner layer. The interior shell ensures that there is substantially no migration of the filler into the foamed inner layer(s) and the outer shell also ensures there is no migration of the filler into the body. Migration of the filler into the body is a matter of concern in the use of such prosthesis.

The filler can assume a porous structure using a similar method to that described in relation to the foamed inner layer above. That can lead to further reduction in the weight of the prosthesis.

Method

The implantable prosthesis of the present invention can be made by foaming the interior shell using, for example, a mould such as a mandrel. Biocompatible filler is then injected into the interior shell. The interior shell is then coated with a foamed inner layer which is then coated with an exterior shell. These steps can be repeated one or more times if desired. The exterior shell of the foamed inner layer is then coated with an outer shell followed by injection of a biocompatible filler between the exterior shell of the foamed inner layer and the outer shell. It is important to ensure that the individual layers are cured prior to coating subsequent layers. The curing can be achieved by allowing each layer to dry at room temperature or higher, for example up to 160° C. When the foamed inner layer is coated, porosity is achieved by use of a blowing agent as described above and then curing the layer.

An exemplary embodiment of the invention will now be described with reference to the following non-limiting drawing and/or example.

BRIEF DESCRIPTION OF THE DRAWING

FIG. 1 is a drawing of a cross-section of an implantable prosthesis according to an exemplary embodiment of the present invention.

In an exemplary embodiment of the invention as shown in FIG. 1, an implantable prosthesis 2 includes an outer shell 4 which may be composed of a silicon-containing material such as silicone or a silicon-containing polyurethane. There is one or more biocompatible filler layer(s) 6 which is typically a gel or a saline solution contained within the outer shell 4. There is one or more foamed inner layer(s) 8 contained within the biocompatible filler layer(s). The biocompatible filler layer(s) 6 have interior shells 10 and exterior shells 12 which may be composed of the same materials as the outer shell 4 thereby substantially preventing the pores of the foam being filled with the biocompatible filler. The foamed inner layer(s) 8 may be composed of the same material as the outer shell which has been made porous by use of a blowing agent such as water or alcohol.

The implantable prosthesis is filled with a biocompatible filler 14 which is typically a gel or saline solution.

EXAMPLE

An embodiment of the invention will now be described with reference to the following non-limiting example.

Different mandrels were manufactured with different radii in a such a way so that a layered breast implant could be made. Four different shells were manufactured, between the first two shells there was a gap of ~0.5 cm and a silicone gel was injected which was subsequently cured. Between the second and third shell there was a larger gap of ~1 cm and silicone foam (as disclosed in U.S. Pat. No. 4,767,794) was injected which foamed to a density of <0.1 g/cc. In the gap between the third and fourth shell a same silicone gel was injected and cured. The layered breast implant had it weight reduced to less than 50% to a similar sized breast implant with a uniform gel filling.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The complete disclosure of all patents, patent documents and publications cited herein are incorporated herein by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

The invention claimed is:

1. An implantable prosthesis comprising:
   (i) an outer shell having an interior surface and an exterior surface, the exterior surface adapted to contact tissue in the body;
   (ii) a biocompatible filler layer of a cured silicone gel contained within the outer shell;
   (iii) a cured foamed inner layer having an interior shell and an exterior shell which prevent the pores of the foam from being filled with the biocompatible filler, the foamed inner layer being contained within the biocompatible filler layer wherein the foam comprises a silicone foam comprising the reaction product of:
      (a) 100 parts by weight of a vinyl-containing polysiloxane of the formula:

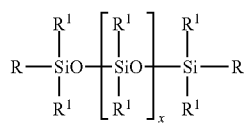

wherein R is vinyl and $R^1$ is methyl, phenyl or 3,3,3-trifluoropropyl, such that the polymer contains from 0.0002 to 3% by weight vinyl and x varies such that the viscosity of the polymer varies from 100 to 1,000,000 centipoise at 25° C.;
      (b) from 5-30 parts by weight of a hydride polysiloxane of the formula:

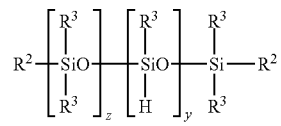

where $R^2$ is selected from the group consisting of, independently, hydrogen, alkyl radicals of from 1 to 8 carbon atoms, aryl radicals of from 1 to 8 carbon atoms, haloalkyl radicals of 3 to 8 carbon atoms and simultaneously, a single —O— to form a cyclic polymer, and $R^3$ is selected from the group consisting of alkyl radicals of from 1 to 8 carbon atoms, aryl radicals of from 1 to 8 carbon atoms, and fluoroalkyl radicals of 3 to 8 carbon atoms, where the hydride polysiloxane has a hydrogen content varying from 0.3 to 1.6% by weight and z and y vary such that the polymer has a viscosity varying from 1 to 500 centipoise at 25° C.;
      (c) a hydroxyl source selected from the group consisting of hydroxylated siloxane, and combinations of hydroxylated polysiloxane with an organic alcohol having from 1-12 carbon atoms in an amount to provide a molar ratio of from about 0.02/1 to about 15/1 of hydroxyl radicals to silicon-bonded hydrogen atoms of component (b);
      (d) from about 1 to about 250 parts per million of platinum catalyst, and optionally;
      (e) an amount of amine compound effective to lower foam density of the formula:

$NR_3^4$ wherein $R^4$ is selected from the group consisting of hydrogen, hydroxy, substituted or unsubstituted alkyl of 1 to 18 carbon atoms and substituted or unsubstituted aryl of 1 to 18 carbon atoms, and a substituted or unsubstituted silyl; and
      (f) optionally, a filler; and
   (iv) repeating layers (ii) and (iii) one or more times if desired; and
   (v) a biocompatible filler contained within the interior shell of the foamed inner layer.

2. A shell for an implantable prosthesis comprising:
   (i) an outer shell having an interior surface and an exterior surface, the exterior surface adapted to contact tissue in the body;
   (ii) a biocompatible filler layer of a cured silicone gel contained within the outer shell; and
   (iii) a cured foamed inner layer having interior shell and an exterior shell which prevent the pores of the foam being filled with the biocompatible filler, the foamed inner layer being contained within the biocompatible filler layer wherein the foam comprises silicone foams comprising the reaction product of:
      (a) 100 parts by weight of a vinyl-containing polysiloxane of the formula:

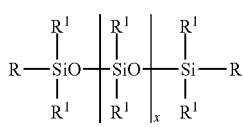

wherein R is vinyl and $R^1$ is methyl, phenyl or 3,3,3-trifluoropropyl, such that the polymer contains from 0.0002 to 3% by weight vinyl and x varies such that the viscosity of the polymer varies from 100 to 1,000,000 centipoise at 25° C.;

(b) from 5-30 parts by weight of a hydride polysiloxane of the formula:

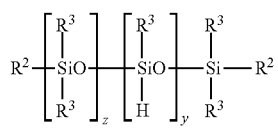

where $R^2$ is selected from the group consisting of, independently, hydrogen, alkyl radicals of from 1 to 8 carbon atoms, aryl radicals of from 1 to 8 carbon atoms, haloalkyl radicals of 3 to 8 carbon atoms and simultaneously, a single —O— to form a cyclic polymer, and $R^3$ is selected from the group consisting of alkyl radicals of from 1 to 8 carbon atoms, aryl radicals of from 1 to 8 carbon atoms, and fluoroalkyl radicals of 3 to 8 carbon atoms, where the hydride polysiloxane has a hydrogen content varying from 0.3 to 1.6% by weight and z and y vary such that the polymer has a viscosity varying from 1 to 500 centipoise at 25° C.;

(c) a hydroxyl source selected from the group consisting of hydroxylated siloxane, and combinations of hydroxylated polysiloxane with an organic alcohol having from 1-12 carbon atoms in an amount to provide a molar ratio of from about 0.02/1 to about 15/1 of hydroxyl radicals to silicon-bonded hydrogen atoms of component (b);

(d) from about 1 to about 250 parts per million of platinum catalyst, (e) optionally, an amount of amine compound effective to lower foam density of the formula:

$NR_3^4$ wherein $R^4$ is selected from the group consisting of hydrogen, hydroxy, substituted or unsubstituted alkyl of 1 to 18 carbon atoms and substituted or unsubstituted aryl of 1 to 18 carbon atoms, and a substituted or unsubstituted silyl; and (f) optionally a filler; and (iv) repeating layers (ii) and (iii) one or more times if desired.

* * * * *